(12) United States Patent
Livingston

(10) Patent No.: US 6,227,047 B1
(45) Date of Patent: May 8, 2001

(54) STRENGTH EVALUATION ISOMETRIC TESTING SYSTEM

(75) Inventor: J. Tracy Livingston, Heber City, UT (US)

(73) Assignee: Zevex, Inc., Salt Lake City, UT (US)

( * ) Notice: Subject to any disclaimer, the term of this patent is extended or adjusted under 35 U.S.C. 154(b) by 0 days.

(21) Appl. No.: 09/020,286

(22) Filed: Feb. 6, 1998

(51) Int. Cl.[7] .................................................. A61B 5/22
(52) U.S. Cl. ............................................... 73/379.08
(58) Field of Search ........................ 73/379.08; 272/134; 482/134, 8; 128/774

(56) References Cited

U.S. PATENT DOCUMENTS

| | | |
|---|---|---|
| 2,140,332 | 12/1938 | Rabkin . |
| 3,752,144 | 8/1973 | Weigle, Jr. . |
| 4,702,108 * | 10/1987 | Amundsen et al. .................... 73/379 |
| 4,742,832 | 5/1988 | Kauffmann et al. . |
| 4,882,677 | 11/1989 | Curran . |
| 4,883,066 | 11/1989 | Widdoes et al. . |
| 4,919,418 | 4/1990 | Miller . |
| 4,939,933 | 7/1990 | Curran . |
| 5,005,140 | 4/1991 | Havriluk . |
| 5,078,152 * | 1/1992 | Bond et al. ........................... 128/774 |
| 5,085,226 | 2/1992 | DeLuca et al. . |
| 5,088,727 * | 2/1992 | Jones ................................... 272/134 |
| 5,174,154 | 12/1992 | Edwards . |
| 5,230,672 | 7/1993 | Brown et al. . |
| 5,398,698 | 3/1995 | Hiller et al. . |
| 5,522,783 | 6/1996 | Gordon . |
| 5,643,161 | 7/1997 | Gordon . |
| 5,762,593 * | 6/1998 | Whiteley ............................... 482/134 |
| 5,800,310 * | 9/1998 | Jones ....................................... 482/8 |

* cited by examiner

Primary Examiner—Benjamin R. Fuller
Assistant Examiner—Jewel V. Thompson
(74) Attorney, Agent, or Firm—Morriss, Bateman, O'Bryant & Compagni

(57) ABSTRACT

An isometric testing apparatus for performing isometric strength tests on individual muscles or joints of a patient includes a base, a seat coupled to the base, a vertical member coupled to the base, a horizontal arm coupled to the vertical member, and a force measuring device coupled to the horizontal arm. The base is configured for conserving space and allowing for placement proximal a corner. The chair is adjustably coupled to the base and may be adjusted to be located within the testing area, outside the testing area, and adjacent the testing area so that the chair may be used as needed or moved out of the way. The force measuring device is adjustably coupled to the base through the horizontal arm and vertical member and is horizontally and vertically adjustable for proper placement of the force measuring device. The force measuring device is pivotally mounted to the horizontal arm and pivots in a vertical plane to correct for any deflection of the vertical arm. The seat is pivotally coupled to the base and the force measuring devise is rotatably coupled to the base so that the seat may be pivoted and the force measuring device rotated so that the patient's joint line of action is parallel with the centerline of the force measuring device.

41 Claims, 8 Drawing Sheets

STRENGTH EVALUATION ISOMETRIC TESTING SYSTEM

BACKGROUND

1. The Field of the Invention

This invention relates to an isometric testing apparatus used in physical therapy for performing isometric strength tests on individual muscles or joints of a patient. More particularly, the present invention is directed to an isometric testing system having a platform upon which the patient may stand; an adjustable and pivoting seat adjusting in and out of a test area and pivoting to orient the patient; an adjustable and pivoting load cell to properly position and orient the load cell; and a plurality of engaging devices detachably coupled to the load cell by quick-connect coupling.

2. The Background Art

Isometric assessment of muscular strength has been employed extensively in orthopedic, sports, rehabilitation, and industrial clinics for more than 40 years. Isometric testing typically involves a maximum voluntary contraction at a specified joint angle or functional position against an unyielding pad or handle connected to a force measuring device. In contrast to isometric testing, isokinetic testing measures strength throughout a range of motion of a body segment using a yielding, constant velocity device to which a force measuring device is attached. The isometric testing modality has become more popular due to the availability of testing products.

The first generation of such isometric testing devices were developed in the early 1980s and involved measurement of only the maximal force using a cable tension meter or dial gauge. The disadvantages of these systems include the ability to measure only gross large forces, poor sensitivity at small forces, and an inability to dynamically measure forces. Additionally, the cable systems were cumbersome, setup times were long, and the number of muscle groups that could be tested was severely limited.

The second generation of these isometric testing devices use computerized testing platforms with a chair utilized for upper and lower extremity bilateral testing, spine evaluations, and lifting assessments. These systems analyze the force curve over time, provide feedback on cogwheeling, measure fatigue, determine rate of contraction, assess consistency of effort, calculate averages, determine bilateral deficit, etc., all relating to the performance of a patient.

One disadvantage of these above-described devices is the nonintegrated test chair. The chairs included in these devices were added as an afterthought. The chairs use considerable floor space due to their size, are heavy, and must be wheeled or carried into place over the platform for use. In addition, the patient must be removed from the chair and the chair moved several times during most exams, making the exam longer and more involved.

Thus, there is a need for a device which more conveniently incorporates a chair for spinal, upper, and lower extremity tests, but still conveniently allows for lift and functional testing of a patient without the chair being a hinderence.

Another disadvantage of these above described devices is that the load cell operates in tension only, requiring multiple setups for antagonist/agonist testing. In order to provide assessments of antagonist/agonist muscle groups, cumbersome cables or straps must be used. After testing the agonists, the patient and chair must be turned around to keep the load cell in tension to test the antagonists, which increases the setup and documentation time considerably. For example, when measuring the biceps, the handle, cable, and transducer are pulled to place them in tension. When measuring the opposite motion (elbow extension using the triceps), however, the patient and chair are turned around to keep the cable/strap in tension. This requires two different setups for the chair and patient. In addition, moving in and out of the chair for every test may prove even more time consuming, burdensome, and painful for injured patients.

Thus, there is a need for a device with a load cell that operates in both tension and compression so that agonist/antagonist muscle assessments may be completed in a single patient position.

Another disadvantage with these above described devices is that they use two-dimensional positioning to orient the load cell with respect to the muscle group being tested, requiring complex bilateral testing setups. The positioning methods of most systems include adjustment of the load cell height, load cell angle in the vertical plane, horizontal distance from the load cell acting point, chair orientation, etc. But in most systems, the direct line of action between the plane of movement of the muscles being tested and the centerline of the transducer results in large errors in maximal force. For example, during a knee flexion test, the patient is seated in a chair and a strap is connected around the leg just above the ankle. The tranducer is lowered so the strap is horizontal. With the patient seated in front of the transducer, the line of action is 24 degrees resulting in a strength measurement error of approximately 10 percent.

Thus, there is a need for a device which provides for more convenient and accurate bilateral testing. In order to solve this problem, some devices move the chair, and the patient, to the right for left side testing and to the left for right side testing. This cumbersome procedure equalizes the line of action for the muscles being tested and the tranducer, but the patient is requires to exit the chair, the chair is moved, and the patient is then repositioned on the chair. If multiple tests are required, the problem is compounded. Thus, there is still a need for a more convenient device for bilateral testing. In addition, there is a need for a device that provides a direct line of action between the transducer and the point line of action.

Another disadvantage of the prior art devices is the decreased repeatability of the tests due to the use of cables and straps. The use of cables and straps makes it difficult to position the patient exactly the same for follow-up tests. Thus, there is a need for a device that eliminates straps and cables to improve the repeatability of follow-up tests.

Another disadvantage in some devices is the requirement for two testing systems, one with a chair for testing the extremities and another with a platform for lift testing. Two devices require additional floor space and expense. Thus, there is a need for a device that requires less floor space and reduces expense but which can perform various different isometric tests on a patient.

An additional disadvantage of the above described devices is that they are unable to meet clinical requirements for functional diagnostic testing or post offer employee testing. Functional diagnostic testing in clinical environments requires a device that may be quickly customized for testing. Post offer employee testing requires objective, baseline, tester independent, easy to administer, standard and job specific isometric strength tests. Current devices were not designed for these emerging uses. Thus, there is still a need for a device that can be quickly customized for different tests and provide objective and easily administered tests.

In view of the above mentioned disadvantages, it would be an advance in the industry to provide an apparatus for isometric testing which overcomes these and other drawbacks.

BRIEF SUMMARY AND OBJECTS OF THE INVENTION

In view of the above described state of the art, the present invention seeks to realize the following objects and advantages.

It is a primary object of the present invention to provide an isometric testing apparatus capable of performing both seated tests, such as spinal, upper and lower extremity tests, and standing tests, such as lifting and functional tests.

It is also an object of the present invention to provide such an isometric testing apparatus which requires minimal space.

It is a further object of the present invention to provide such an apparatus which allows the position of the patient to be easily adjusted.

It is a further object of the present invention to provide an isometric testing apparatus capable of performing agonist/antagonist muscle tests in one patient position.

It is a further object of the present invention to provide an isometric testing apparatus capable of creating a direct line of action between the centerline of the force measuring device and the joint line of action of the patient.

It is a further object of the present invention to provide an isometric testing apparatus capable of providing a reproducible method of recording the position of the patient and force measuring device.

It is a further object of the present invention to provide an isometric testing apparatus capable of providing a force measuring device with a line of action the same as the patient's line of action, even if the structure of the apparatus deflects during the testing.

It is a further object of the present invention to provide an isometric testing apparatus that can be quickly customized.

These and other objects and advantages of the invention will become more fully apparent from the description and claims which follow, or may be learned by the practice of the invention.

The present invention provides an isometric testing apparatus for performing isometric strength tests on individual muscles or joints of a patient. The apparatus generally includes a base, a seat coupled to the base, a vertical member attached to the base, a horizontal arm coupled to the vertical member, and a force measurement device coupled to the horizontal arm.

The base is adapted for resting on an underlying surface, such as the ground or the floor. The base has a platform upon which a patient may stand or otherwise be disposed during testing. The platform has a patient area upon which the patient may be disposed either standing or sitting. An area or volume extending vertically from the patient area defines a testing area in which the patient is disposed during testing. The seat has a seat member upon which the patient may sit and a back portion. The seat member and back portion form support surfaces against which the patient may push during testing.

The force measuring device may be a load cell, transducer, or other device available in the industry. The force measuring device preferably transforms the force applied to the load cell by the patient into an electrical signal which may be displayed or stored.

The vertical member and horizontal arm support the force measuring device. The vertical member is preferably strong enough to resist deflection as the patient pushes against the load cell, and thus the vertical member. The vertical member is also preferably smooth and cylindrical. Similarly, the horizontal arm is preferably strong enough to resist deflection.

In accordance with one aspect of the present invention, the base is preferably shaped or configured to allow the apparatus to be located proximal a corner of a room as well as proximal a wall. The base has two deeply chamfered corners creating a corner portion that may be positioned in a corner of a room. Thus, the apparatus of the present invention advantageously conserves floor space.

In accordance with another aspect of the present invention, the platform has a grid pattern and/or indicia formed thereon for documenting and orienting the patient's foot position. By recording the position of the patient on the platform, the test may be reliably repeated at a later time, such as during a follow up test.

In accordance with another aspect of the present invention, the seat is adjustably coupled to the base for providing easy adjustment between various testing configurations and providing a support surface against which the patient may push. The seat adjusts between at least a first test position, where the seat is located within the test area and where the seat receives a body part of the patient and an idle position, where the seat is located outside of the test area and where the seat does not contact the patient. In addition, the seat may be adjusted to multiple locations including a second test position, where the seat is located adjacent the test area so that the patient may stand on the platform and push against the seat. Therefore, the seat may be easily and quickly adjusted in accordance with the requirements of the test to be performed. Because the seat is coupled to the base, it may be used as a support surface against which the patient may push. In addition, because the seat is adjustable to a position outside of the test area, it may be easily moved out of the way for tests in which it is not required.

In accordance with another aspect of the present invention, the horizontal arm is adjustably coupled to the vertical member by a coupling member for properly positioning the force measuring device. The horizontal arm and coupling member slide vertically along the length of the vertical member. The horizontal arm, and thus the force measuring device, may be vertically positioned between at least a first elevation near the base and a second elevation farther from the base. Therefore, the load cell may be vertically positioned as required by the test being performed.

In addition, the horizontal arm moves horizontally with respect to the coupling member and the vertical arm. The horizontal arm, and thus the force measuring device, may be horizontally positioned between at least a first position near the vertical member and a second position farther from the vertical member. Therefore, the load cell may be horizontally positioned as required by the test being performed.

In accordance with another aspect of the present invention, the force measuring device, or load cell, functions in both tension and compression modes for performing agonist/antagonist tests. Therefore, the patient may push against the load cell for an extension test and then pull against the load cell for a flexion test without the patient being repositioned.

In accordance with another aspect of the present invention, the force measuring device, or load cell, is pivotally coupled to the horizontal arm and pivots in a vertical plane for properly orienting the load cell. In addition, the load cell preferably pivots freely to compensate for any deflection of the horizontal arm and vertical member during testing. Because the load cell pivots, it may be oriented so that the patient's line of action is parallel with the centerline of the load cell. Therefore, the force measurements made by the present apparatus will be accurate.

In accordance with another aspect of the present invention, the seat is pivotally coupled to the base and the horizontal arm, and thus the force measuring device is rotatably coupled to the vertical member for providing a direct line of action between the patient's joint line of action and the centerline of the load cell. The seat may be pivoted and the load cell rotated so that the patient's joint line of action is parallel with the center line of the load cell. Therefore, the force measurements will be more accurate. In addition, a test may be first performed on a patient's left side, then the seat may be pivoted and the load cell rotated to perform the same test on the patient's right side. Therefore, bilateral testing may be quickly and easily performed on a patient.

In accordance with another aspect of the present invention, a plurality of engagement devices are provided with quick connect/release fittings for attachment to the load cell. The engagement devices are acted upon by the patient and transfer the force applied by the patient to the load cell. The engagement devices may be acted upon by pulling, pushing, lifting, etc. The engagement devices may include a long lift bar, a short lift bar, a handle, a cable, a pad, or a pad with a strap. The engagement device is detachably coupled to the load cell by a quick connect/release coupling so that the various engagement devices may be quickly and easily interchanged for different test configurations.

In accordance with another aspect of the present invention, the force measuring device is coupled to a computer for displaying and storing the measured forces. The computer may also have a software program for prompting the various testing configurations based on standard or customized tests.

BRIEF DESCRIPTION OF THE DRAWINGS

In order to better appreciate how the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Reference will now be made to the drawings wherein like structures will be provided with like reference designations.

Figure 1:
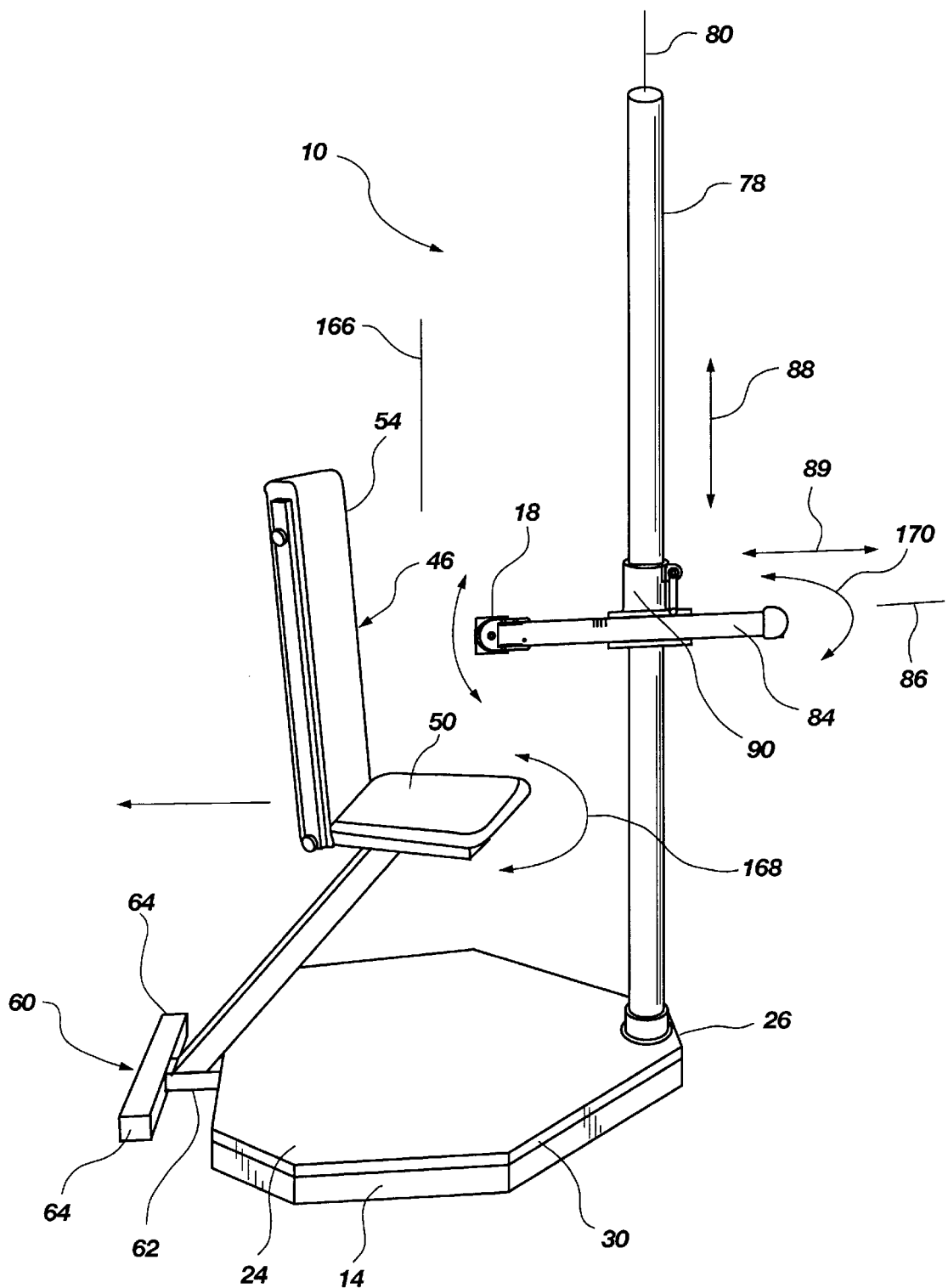
FIG. 1 is a perspective view of a presently preferred embodiment of an isometric testing apparatus of the present invention.
Figure 2:
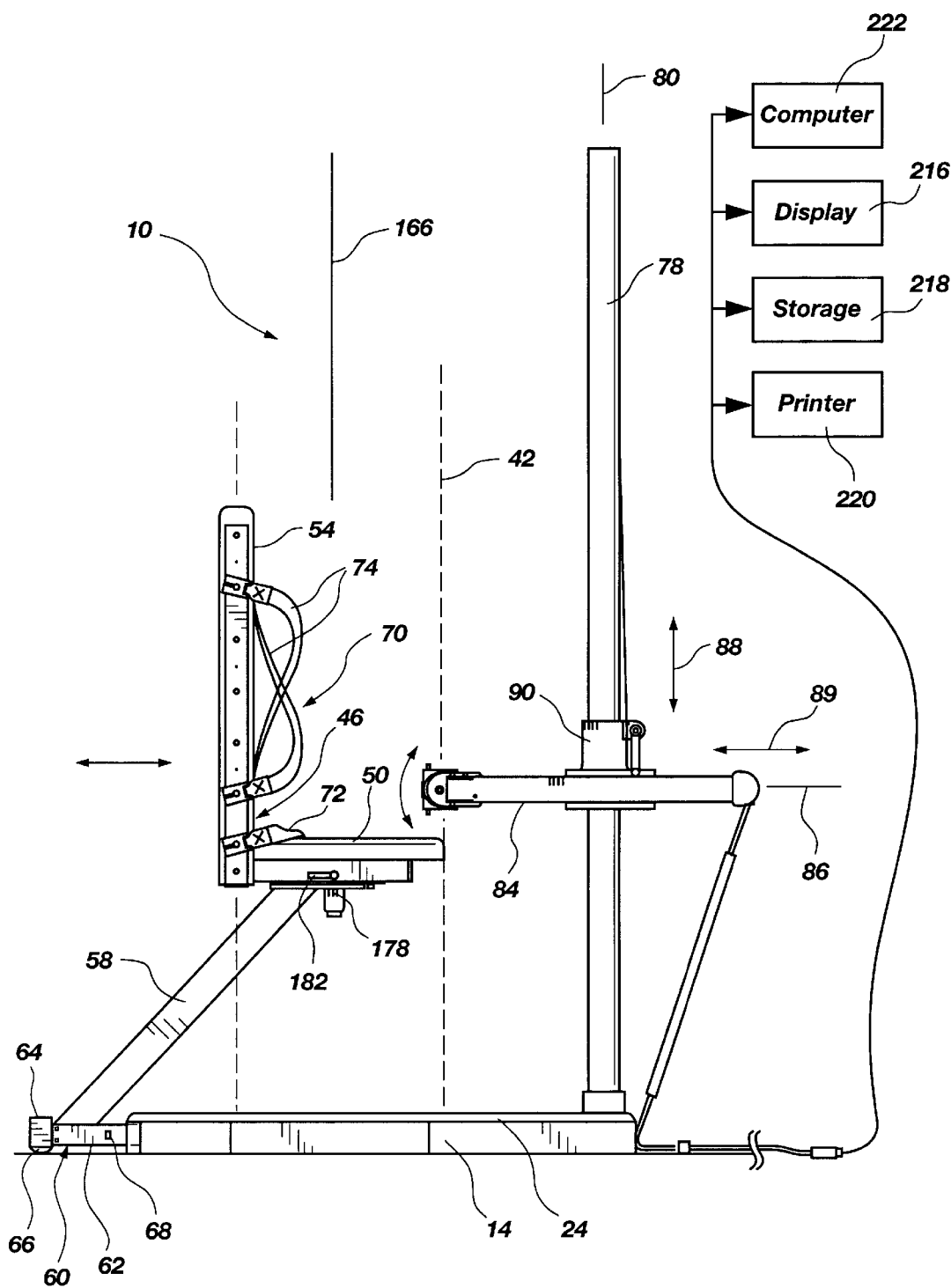
FIG. 2 is a side view of the presently preferred embodiment of the isometric testing apparatus of the present invention.

Reference will first be made to FIGS. 1 and 2 which are a perspective view and a side view, respectively, of an isometric testing apparatus in accordance with the present invention, generally designated at 10. The apparatus 10 is used to perform isometric strength tests on individual muscles or joints of a patient. Thus, the apparatus 10 interfaces with various body parts of the patient, such as the patient's hands, arms, knees, legs, buttocks, and back, as will be discussed more fully below. It is of course understood that numerous isometric tests may be performed involving numerous parts of the patient's body. Only a few of the many possible tests will be illustratively discussed below.

The apparatus 10 is designed to be disposed on a flat, horizontal surface and is particularly well suited for use in physical therapy clinics or in workplace clinics, but can be used in many other settings. While the clinics are examples of the type of settings which can currently best benefit from the present invention, it will be appreciated, however, that other types of facilities or situations, for example hospitals, can benefit from embodiments of the present invention. The isometric testing apparatus 10 generally includes a base member, a seat, a force measuring device, a support structure, and means for adjusting the position of the force measuring device, all of which will be discussed in greater detail below.

The isometric testing apparatus 10 includes a base or base member 14 which is adapted for resting on an underlying surface, such as the ground, a floor, flat horizontal surface, or some other appropriate surface. The base member 14 advantageously has a platform 24 or surface upon which a patient may be disposed. Preferably the platform 24 is horizontal and able to receive the patient in a standing position. The base may be a structural member supporting the platform or the base and platform may be formed as an integral unit. The base and platform provide a surface upon which the patient may be disposed or upon which the patient may stand.

Referring now to FIG. 1, the platform 24 and base 14 advantageously are shaped or configured to provide a stable base that conserves space. The shape of the base 14 and platform 24 may be described as a square with chamfered or angled corners, or as an octagon with equal or unequal sides, or as a diamond. The base 14 preferably has at least two deeply chamfered corners forming a corner end, indicated at 26. The chamfered square configuration allows the base and platform to be positioned in a corner as well as along a wall. Thus, the apparatus may be positioned as desired without wasting space or having the apparatus project unsafely or inconveniently placed into a workspace.

In addition, the base 14 and platform 24 are preferably sized to provide an adequate support structure while at the same time occupying a minimal amount of space. The platform 24 must be wide enough for a patient to stand or sit on and for preventing the apparatus from being overturned or unstable. But the base 14 must also be narrow enough to be located as desired while conserving space and remaining compact. Preferably the base and platform are about four feet wide and about four feet long.

The platform 24 preferably has a non-skid surface to prevent the patient from slipping. Those skilled in the art can arrive at many different techniques for providing a nonskid surface on the platform 24. In addition, a grid pattern and/or indicia 30 advantageously are formed on the platform 24 or surface. The grid pattern 30 preferably includes a first array of parallel lines spaced from a point associated with a force measurement device and a second array of lines radiating from the point associated with the force measurement device, as shown in FIG. 1. Thus, the lines form a plurality of various shaped quadrilateral zones. The first array of lines indicate the distance of the patient's foot from the point while the second array of lines indicates the distance and/or angle of the foot with respect to the point. The indicia are associated with the lines and may indicate such information as distance from the point, the angle formed with respect to the point, a particular zone, and the like.

The grid pattern and indicia 30 allow the foot position of the patient to be documented. In addition, particular test may be repeated with accuracy because the patient's feet may be repositioned as documented in prior tests. It is of course understood that the grid and indicia may also be used to document other information and reposition other objects or body parts, such as the location of wheelchair wheels for patients confined to wheelchairs.

As indicated above, the platform 24 is configured or adapted for receiving a patient or having a patient disposed thereon.

Figure 3A:
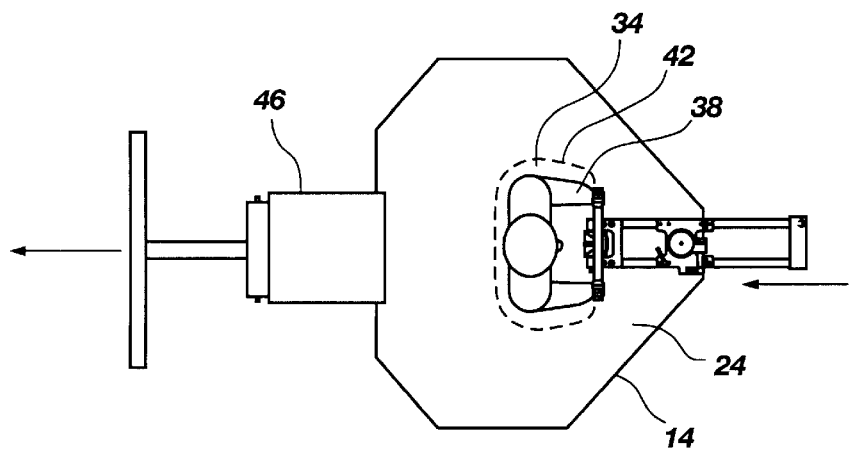
FIG. 3a is a top view of the presently preferred embodiment of the isometric testing apparatus of the present invention with a patient standing thereon and a seat member positioned out of the way.
Figure 3B:
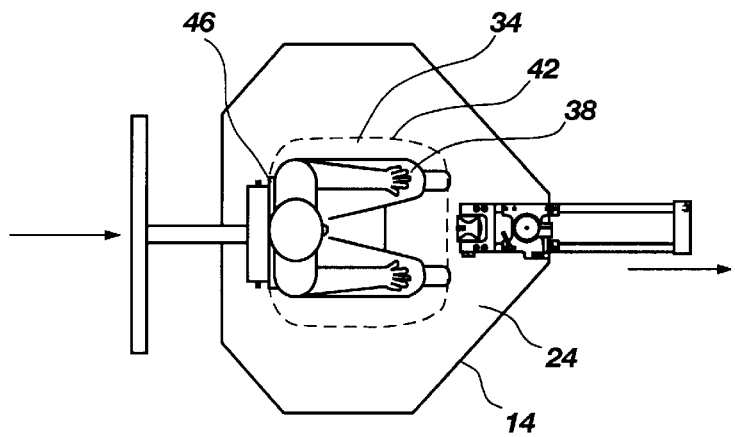
FIG. 3b is a top view of the presently preferred embodiment of the isometric testing apparatus of the present invention with the patient seated on the seat member.
Figure 3C:
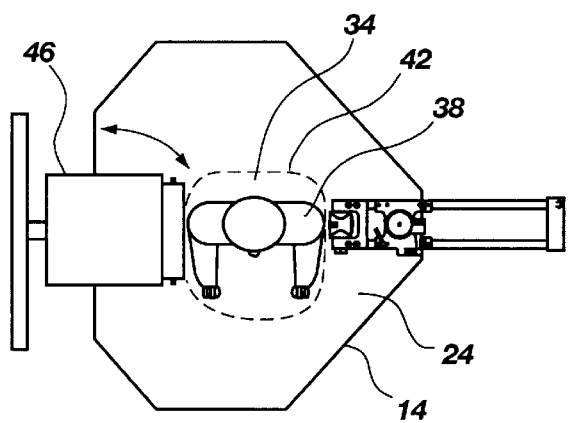
FIG. 3c is a top view of the presently preferred embodiment of the isometric testing apparatus of the present invention with the patient standing thereon and the seat member disposed adjacent the patient for support.

Referring now to FIGS. 3a, 3b and 3c, the platform 24 has a patient area 34 upon which the patient 38 may be disposed. The patient 38 may be standing on the platform in the patient area 34, as shown in FIGS. 3a and 3c, or the patient 38 may be seated in the patient area 34, as shown in FIG. 3b.

Referring now to FIG. 2, an area extending vertically or upwardly from the patient area 34 defines a testing area 42 or volume in which the patient is disposed during testing. The size of the patient area 34 and/or testing area 42 may vary depending on the test being performed and may include all or substantially all of the platform.

Referring again to FIGS. 1 and 2, the apparatus 10 advantageously includes a seat 46 adjustably coupled to the base 14. Preferably, the seat 46 is disposed generally opposing a force measuring device as discussed below. The seat 46 has a seat member 50 for receiving a body part of the patient, such as the patient's buttocks. During most tests utilizing the seat, the patient will be seated upon the seat member. The patient, however, may be disposed on the seat in other positions depending on the test being performed.

In addition, the seat also has a back member 54 for receiving another body part of the patient, such as the patient's back. The back member 54 is preferably disposed perpendicularly to the seat member. The seat member and back member of the seat provide support surfaces against which the patient may push during testing.

The seat 46 advantageously is adjustable between at least a first test position, as shown in FIG. 3b, and an idle position, as shown in FIG. 3a. As shown in FIG. 3b, the seat is adjustable to a position where the seat is located within the test area 42 with a body part of the patient disposed in the seat member, defining the first test position. As shown in FIG. 3a, the seat is adjustable to a position where the seat is located outside of the test area and in which the seat does not contact the patient, defining the idle position. In the first test position, the seat 46 may be disposed over, or on, the platform so the patient may be seated during the test. In the idle position, the seat is disposed out of the way of the patient during the test. The seat may also be adjusted between various other positions to properly position the patient. Therefore, the seat may be easily adjusted between testing configurations.

Referring to FIG. 3c, the seat advantageously is adjustable to a second test position. In the second test position the seat is located adjacent the test area. With the seat in the second test position, adjacent the test area 42, the patient 38 may stand on the platform 24, but still push against the reverse surface of the back member of the seat 46. Preferably, the seat 46 is advantageously pivotally coupled to the base 14 so that the back member of the seat may be positioned towards the base and the patient. The seat may be pivoted 180 degrees so that the back member forms a support surface against which the patient may push.

Referring again to FIG. 1, the seat 46 may include a T-shaped base 60 with a sliding leg 62 in sliding engagement with the base 14. The sliding leg 62 maintains the seat 46 coupled to the base 14 even when the seat is adjusted to the idle position. The sliding leg 62 may be slidingly disposed within a track (not shown) or the like formed in the base 14 for guiding the sliding leg and facilitating movement of the seat as it adjusts between positions.

The T-shaped base 60 also has a pair of lateral legs 64 providing lateral support. A pair of wheels or rollers 66, on of which is shown in FIG. 2, may be disposed on the ends of the lateral legs to facilitate movement of the seat between positions. The seat may be attached to the T-shaped base 60 by an angled member 58 extending from the seat 46 of seat member 50 to a point proximal the intersection between the lateral legs 64 and the sliding leg 62, thus permitting most of the T-shaped base to be slid into the base 14 as the seat is slid towards the base. Indicia 68 may be formed on the top and/or sides of the sliding leg 62 so that the position of the seat may be documented and repositioned.

Referring again to FIG. 2, the seat may also include restraining devices, generally indicated at 70, for stabilizing the patient in the seat and isolating a particular muscle being tested. The restraining devices 70 may be seat belts, harnesses, or the like. The restraining devices are configured to pass around the patient and couple to opposing sides of the seat. As illustrated, the restraining devices preferably include a lap belt 72 configured to pass over the patient's lap and coupled to opposing sides of the seat member, or the lower, opposing sides of the back member. In addition, the restraining devices preferably include a pair of shoulder belts 74 configured to pass over the patient's chest forming a cross, or "X", and each coupled to opposing sides of the back member 54.

Referring again to FIGS. 1 and 2, the apparatus 10 also includes a vertical member 78, mast, or pole coupled to the base 14. The vertical member 78 extends upwardly from the base and defines a substantially vertical axis 80. The vertical member 78 supports and facilitates positioning of a force measuring device as discussed further below. The vertical member 78 is preferably made of a strong, rigid is material to resist bending or breaking. In addition, the vertical member is preferably cylindrical and has a smooth surface, the purpose of which will be discussed further below.

The apparatus 10 advantageously has a horizontal arm 84 adjustably coupled to the vertical member 78 and defining a generally horizontal axis 86. The horizontal arm 84 vertically adjusts along the vertical member 78 between at least a first elevation and a second elevation, as indicated by the arrow 88. The first elevation may be proximal the platform for positioning the force measuring device near the ankle of the patient. The second elevation may be farther from the platform for positioning the force measuring device nearer the arm or shoulder of the patient. The horizontal arm may be adjusted between a plurality or infinite number of elevations to properly position the force measuring device for the test being performed or the muscle or joint being tested.

The horizontal arm 84 advantageously horizontally adjusts along the horizontal axis 86, which is generally parallel with the horizontal arm. The horizontal arm adjusts between at least a first position and a second position, as indicated by the arrow 89. The first position may be near the vertical member, as shown in FIGS. 3b and 3c. The second position may be farther from the vertical member, as shown in FIG. 3a. The horizontal arm may be adjusted between a plurality or infinite number of positions or proximities with respect to the patient to properly position the force measuring device for the test being performed of the muscle or joint being tested.

The vertical member is described above and illustrated in the drawings as comprising a single pole or mast. Likewise, the horizontal arm is described and illustrated as comprising a pair of rods or tubes. It is of course understood that there are various ways of constructing the vertical member and horizontal arm. The vertical member may be formed by a plurality of vertical poles. In addition, the vertical member may be circular, or may have a beam configuration, such as an I-beam or box beam. Likewise, the horizontal arm may be formed by a single rod. In addition, the horizontal arm may also have a beam configuration.

Figure 4:
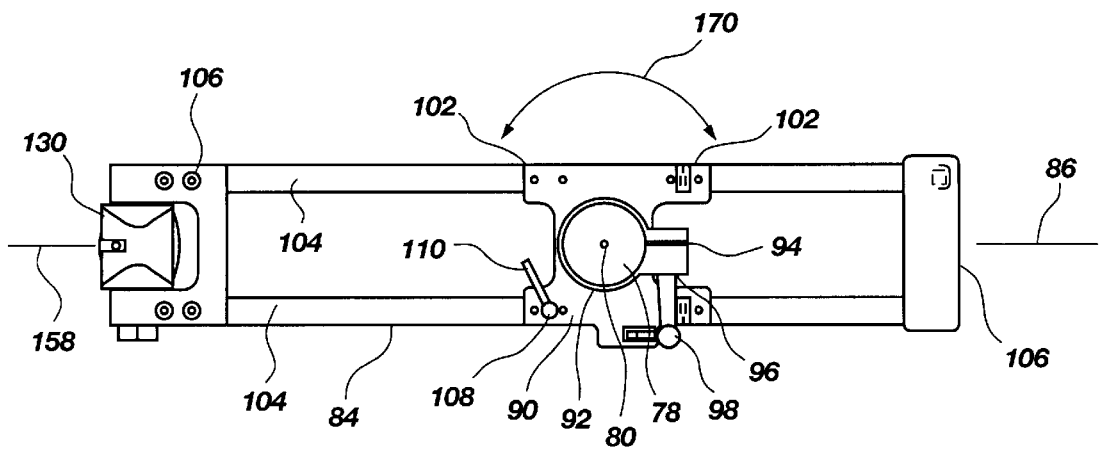
FIG. 4 is a top view of the presently preferred embodiment of a horizontal member of the isometric testing apparatus of the present invention.
Figure 5:
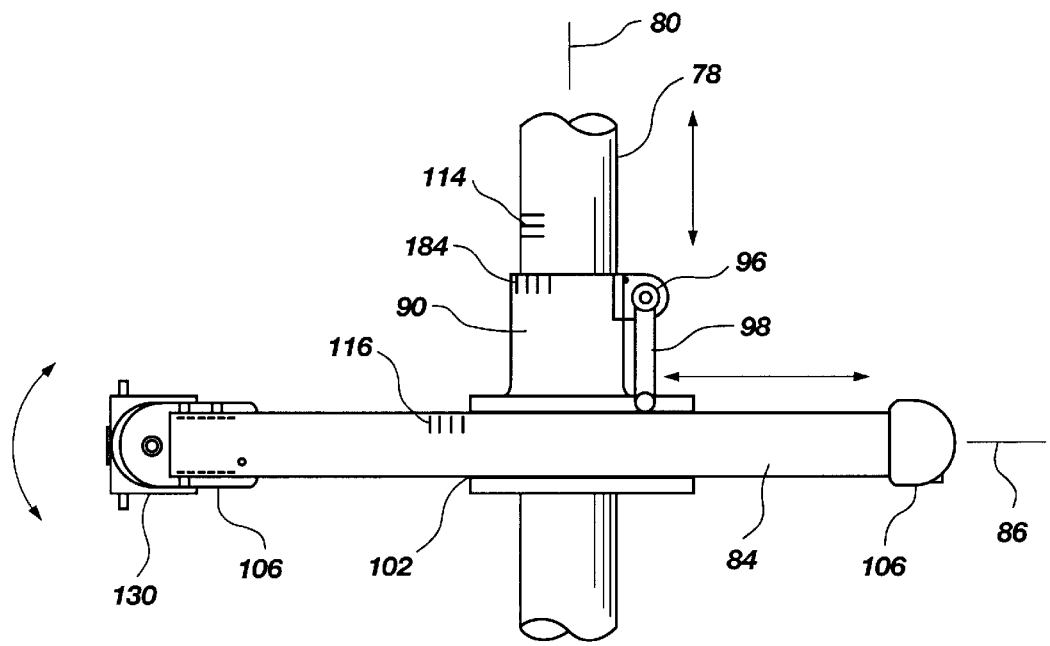
FIG. 5 is a side view of the presently preferred embodiment of the horizontal member of the isometric testing apparatus of the present invention.

Referring now to FIGS. 4 and 5, a coupling member 90 is disposed between and is adjustably coupled to the horizontal arm 84 and the vertical member 78. The coupling member 90 is slidingly disposed on the vertical member 78 and moves up and down, or adjusts vertically, with the horizontal arm 84. The horizontal arm 84 is slidingly disposed in the coupling member 90 and moves back and forth, or adjusts horizontally, with respect to both the coupling member and the vertical member.

The coupling member 90 has a bore 92 extending vertically therethrough for receiving the vertical member 78, as shown in FIG. 4. A slot 94 extends through a portion of the coupling member 90 to a portion of the bore 92. The slot 94 allows inner diameter of the bore 92 to be changed, or allows the bore 92 to be tightened and loosened about the vertical member. A gripping bore 96 passes through the slot 94 and the two portions of the coupling member formed on either side of the slot, the bore in one portion of the coupling member being threaded. A lever arm 98 is disposed in the gripping bore 96 and has a threaded end threadedly engaging the threaded portion of the bore. Thus, the lever arm 98 may be rotated to loosen or tighten the bore 92 about the vertical member 78.

By turning the lever arm to loosen the bore 92, the coupling member 90, and thus the horizontal arm and force measuring device, may be vertically adjusted along the length of the vertical member. When the horizontal arm is positioned vertically as desired, the lever arm 98 may be turned to tightened the bore, thus securing the coupling member 90 to the vertical member. As indicated above, the vertical member may be configured with any number of vertical members and have various configurations. Therefore, the bore may be configured to suit the number and shape of the vertical members.

The coupling member 90 has a slot 102 or groove formed horizontally on each side thereof for receiving the horizontal arm 84, or each of the bar members 104 of the horizontal arm. The bar members 104 of the horizontal arm are maintained in the slots 102 because the bars 104 are maintained equidistance and parallel to one another by end pieces 106. A threaded bore 108 passes through the coupling member 90 and into one of the slots or grooves 102, as shown in FIG. 4. A threaded lever arm 110 is disposed in the threaded bore 108, as shown in FIG. 4. The end of the threaded lever arm 110 bears against the rod member 104 disposed in the slot 102 to prevent movement. Thus, the threaded lever arm 110 may be rotated to bear against or to not bear against the rod member 104.

By turning the lever 110 arm to not bear against the rod member 104, the rod member and horizontal arm, may be horizontally adjusted. When the horizontal arm is positioned horizontally as desired, the lever arm 110 may be turned to bear against the rod member 104, thus securing the horizontal arm 84 to the coupling member 90 and to the vertical member. As indicated above, the horizontal arm may be configured with any number of rod members and have various configurations. Therefore, the slots or grooves may be configured to suit the number and shape of the rod members.

The coupling member and horizontal arm are one example of means for horizontally and vertically positioning or adjusting the load cell. It is of course understood that many different structures or methods may be used to adjust the load cell and the means for horizontally and vertically positioning the load cell are intended to encompass all such structures and are to be considered equivalent to all such strutures. In addition, although the load cell has been described as adjusting with respect to the patient, the patient may be adjusted with respect to the load cell, such as by moving the platform and/or seat.

Referring to FIG. 5, indicia 114 may be formed on the vertical member 78 to indicate the vertical position or elevation of the coupling member 90, horizontal arm 84, and force measuring device. Indicia 116 may also be formed on the horizontal arm to indicate the horizontal position.

As discussed generally above, the apparatus 10 also includes a force measuring device. The force measuring device measures the force applied by the patient. The force measuring device is operatively coupled to the base 14 by the vertical member 78 and horizontal arm 84. The force measuring device 18 is acted upon by a body part of the user, for example, the arm or leg of the patient. The force measuring device may be a load cell, transducer, or the like. Preferably, the force measuring device converts the force applied by the patient into an electrical signal which may be used by a display device or computer as discussed below. Alternatively, the force measuring device may convert the applied force into any other means, such as a dial indicator.

Figure 6A:
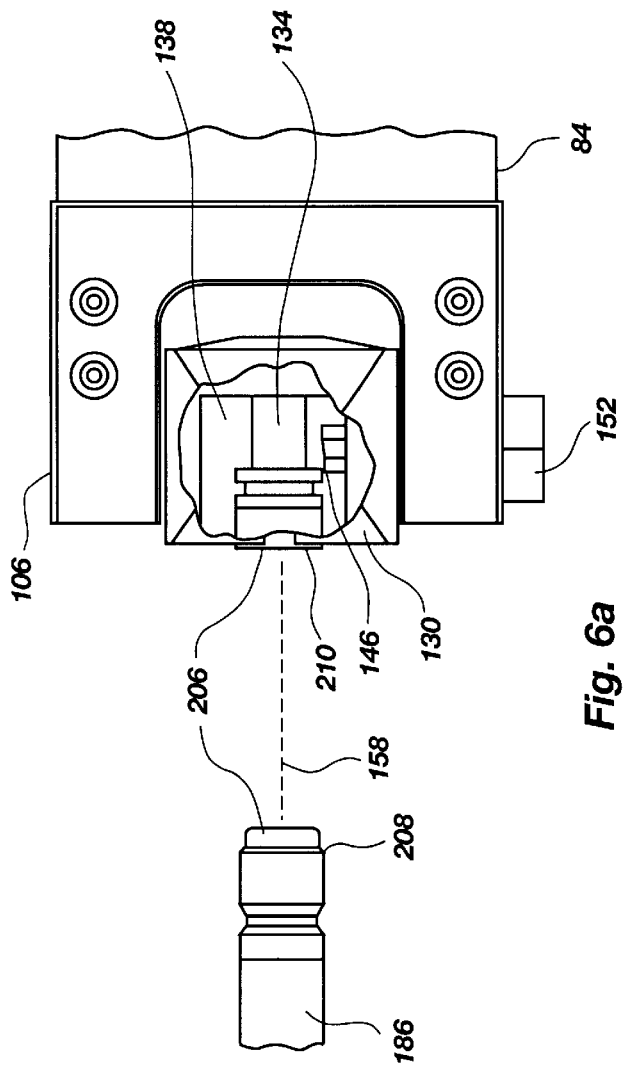
FIG. 6a is a top view of a load cell head of the presently preferred embodiment of the isometric testing apparatus of the present invention with a portion broken away to expose a load cell and quick connect/release coupling of the present invention.
Figure 6B:
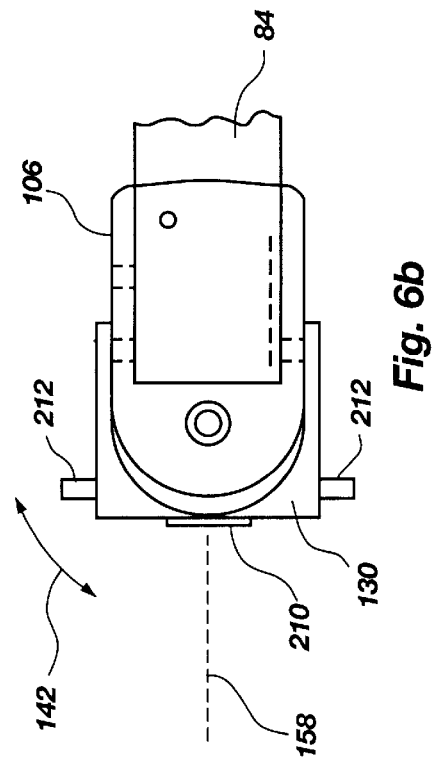
FIG. 6b is a side view of the load cell head of the presently preferred embodiment of the isometric testing apparatus of the present invention.
Figure 6C:
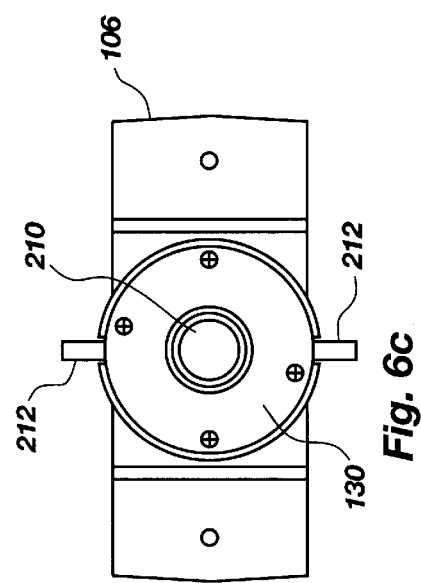
FIG. 6c is a front view of the load cell head of the presently preferred embodiment of the isometric testing apparatus of the present invention.

Referring to FIGS. 6a, 6b and 6c, the force measuring device 18 may include a load cell head or transducer head 130 coupled to the horizontal arm 84 and/or end piece 106. The load cell head 130 provides a housing for the load cell 134, which is disposed within a cavity 138 in the load cell head 130, as shown in FIG. 6a. Because the load cell head 130, and thus the load cell 134, is coupled to the horizontal arm 84, the load cell 134 is horizontally 89 and vertically 88 adjustable, as described above. Thus, the load cell 134 may be properly positioned with respect to the patient.

In addition, the load cell head 130, and thus the load cell 134, advantageously is pivotally coupled to the horizontal arm 84 and pivots in a vertical plane, as indicated by the arrow 142 in FIG. 6b. The pivoting load cell allows the load cell to be properly oriented with respect to the patient. The load cell head 130 and load cell 134 may be fixed with respect to the arm. A threaded bolt 146 passes through the load cell head 130 and the end piece 106 where a knob 152 threadingly engages the bolt. By tightening the knob 152, the load cell head 130 and load cell 134 may be fixed with respect to the horizontal arm. Conversely, by loosening the knob 152, the load cell head and load cell are free to pivot.

Figure 7:
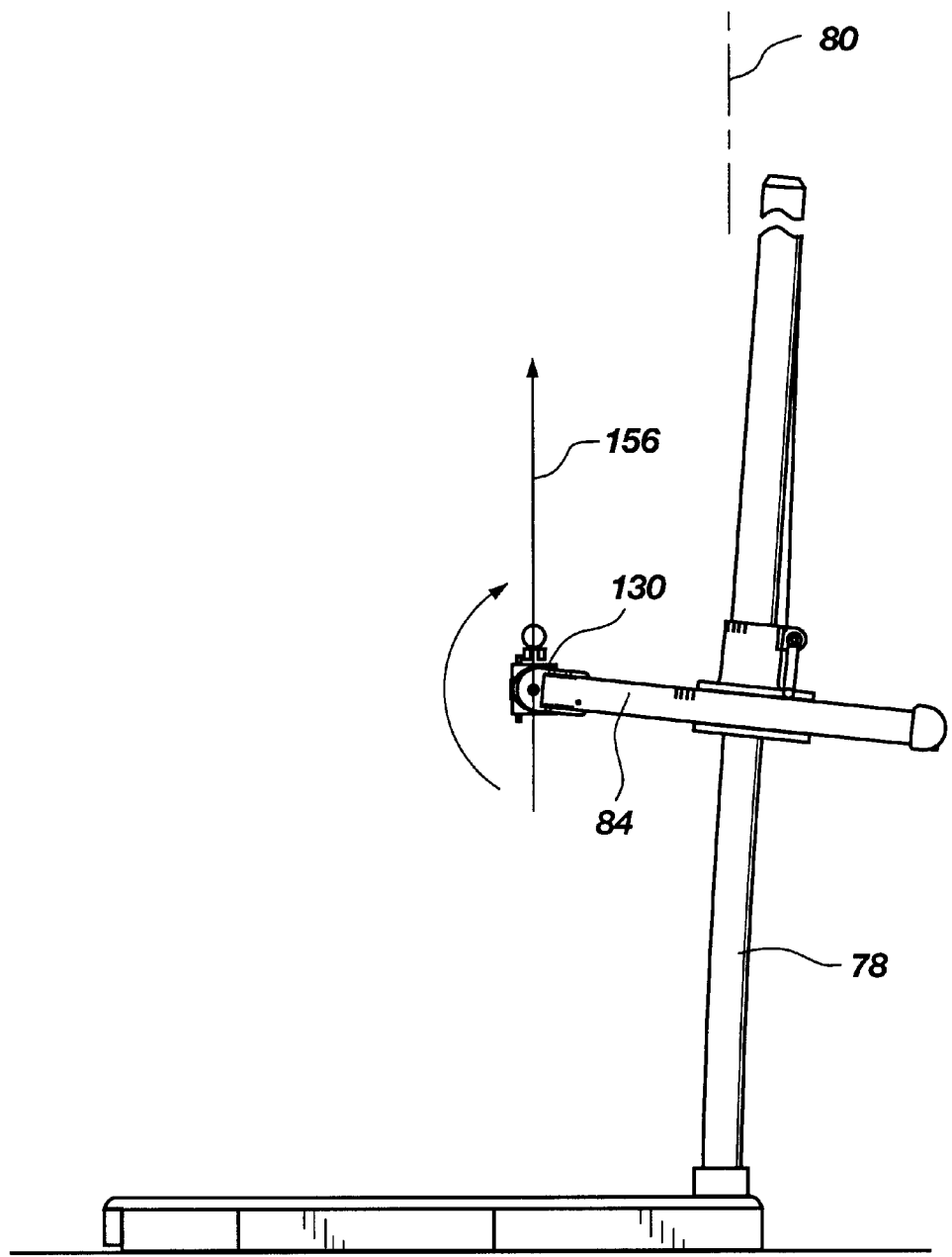
FIG. 7 is a side view of an isometric testing apparatus with a freely pivoting force measuring device compensating for deflection of the apparatus.

Referring now to FIG. 7, the load cell head and load cell preferably pivot freely with respect to the horizontal arm. The pivoting load cell not only allows for initial proper orientation of load cell with respect to the patient, but also compensates any deflection of the horizontal arm 84 or vertical member 78. For example, if the patient exerts an upward force on the load cell in a vertical direction, a vertical line of action is created, as represented by the arrow 156. The force exerted by the patient on the load cell is transferred to the horizontal arm 84 and vertical member 78. The force causes the vertical member and horizontal arm to deflect slightly, as illustrated in FIG. 7. The deflection of the vertical member in FIG. 7 is exaggerated for clarity.

If the load cell is fixed with respect to the horizontal arm and vertical member, the load cell will deflect as the arm and vertical member deflect. As the load cell deflects, the center line of the load cell also deflects so that it is no longer parallel with the line of action 156 of the patient. Because the line of action is no longer parallel with the center line of the load cell, the actual force applied by the patient may be described as composed of two components, a force vector parallel with the centerline of the load cell and a force vector tangent to the centerline.

Because the load cell only measures the force parallel to the centerline, the measured force will be less than the actual force applied. Thus, fixing the load cell to the arm and vertical member introduces an error component. The freely pivoting load cell of the present invention solves this problem because the centerline of the load cell will always freely pivot to be parallel with the line of action of the patient.

Figure 8B:
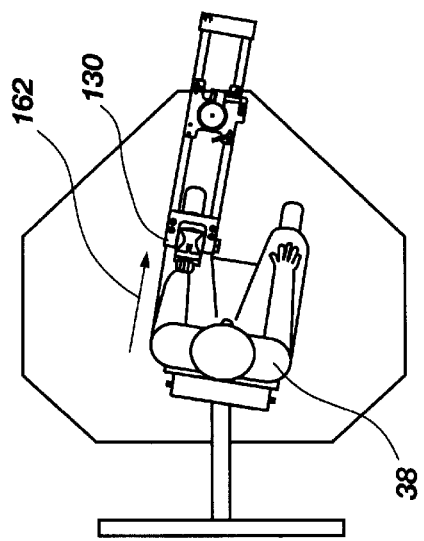
FIG. 8b is a top view of the presently preferred embodiment of the isometric testing apparatus of the present invention with the patient pushing against the load cell.
Figure 8A:
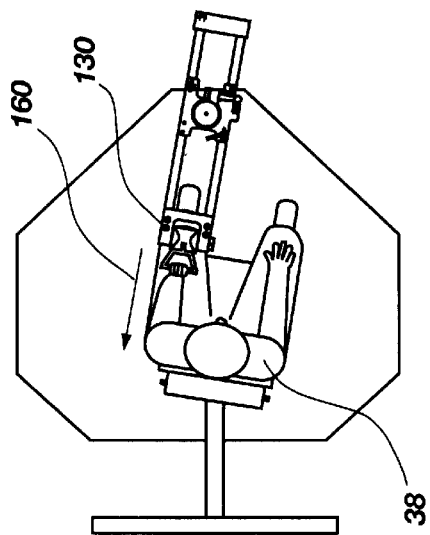
FIG. 8a is a top view of the presently preferred embodiment of the isometric testing apparatus of the present invention with the patient pulling against the load cell.

Referring now to FIGS. 8a and 8b, the load cell 134 preferably functions in both tension and compression. Thus, the patient can push against the load cell or pull away from the load cell depending on the test. Therefore, the apparatus may be used for agonist/antagonist testing while the patient is in a single position. This reduces the time necessary to complete a test, and is easier on disabled patients who have a difficulty moving or being moved. For example, when measuring elbow flexion and extension, the patient is positioned as shown in FIG. 8a. For elbow flexion, the patient pulls against the load cell, as indicated by the arrow 160. For elbow extension, the patient pushes against the load cell, as indicated by the arrow 162. Prior art devices required the patient to first perform the elbow flexion by pulling against the load cell, moving off of the chair, turning the chair around, resitting on the chair, and performing the elbow extension by again pulling against the load cell.

Figure 9B:
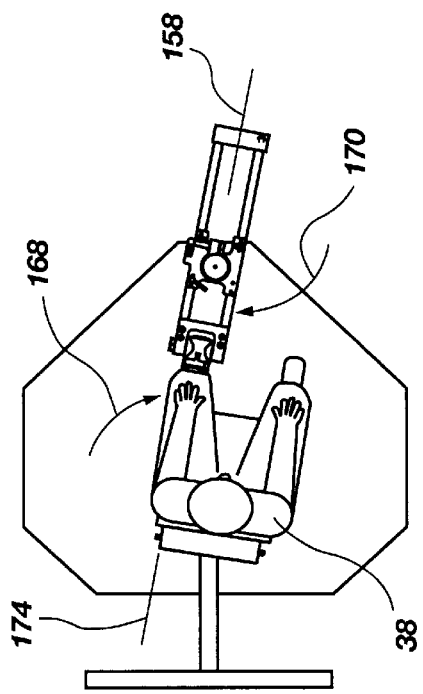
FIG. 9b is a top view of the presently preferred embodiment of the isometric testing apparatus of the present invention with the patient seated on a pivoted seat and the load cell rotated to create a direct line of action between the patient's joint line of action and a centerline of the load cell.
Figure 9A:
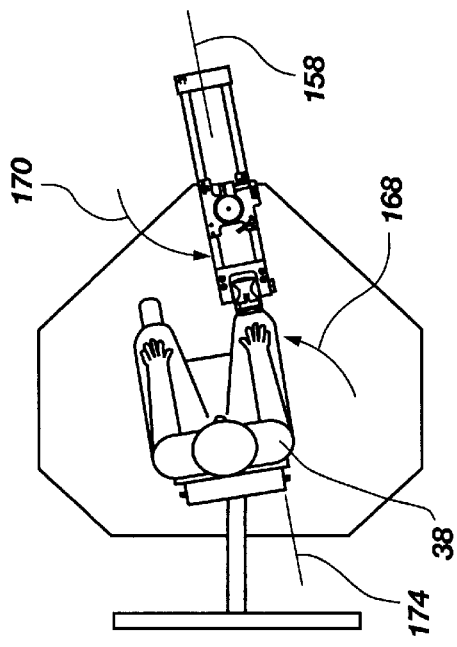
FIG. 9a is a top view of the presently preferred embodiment of the isometric testing apparatus of the present invention with the patient seated on a pivoted seat and the load cell rotated to create a direct line of action between the patient's joint line of action and a centerline of the load cell.

As discussed above, the seat 46 advantageously pivots so that the back member 54 of the seat forms a support surface against which the patient may push. In addition to pivoting 180 degrees, the seat 46 also advantageously pivots in smaller increments about a vertical axis 166, as indicated by the arrow 168 in FIGS. 1 and 2. In addition, the load cell advantageously rotates about the vertical member 78 or vertical axis 80, as indicated by the arrow 170 in FIGS. 1 and 4. Referring now to FIGS. 9a and 9b, the seat 46 pivots 168 and the load cell rotates 170 to create a direct line of action between the centerline 158 of the load cell and a joint line of action 174 of the patient.

For example, in bilateral testing of knee extension, the patient and chair may be pivoted 10 degrees and locked into position, as shown in FIG. 9a. The load cell is then rotated in line with the upper leg and positioned just above the ankle, again as shown in FIG. 9a. The joint line of action 174 of the patient's right knee is parallel with the centerline 158 of the load cell. Referring to FIG. 9b, the chair may then be pivoted the opposite direction and locked in place. The load cell is then rotated in the opposite direction and appropriately positioned. The joint line of action 174 of the patient's left knee is now parallel with the centerline 158 of the load cell.

Because the testing is always in the line of action of the joint, the accuracy of the test is enhanced. In addition, by pivoting the seat and rotating the load cell, the different test configurations may be quickly and easily changed. Furthermore, the patient is not required to move out of the chair as the chair is pivoted, thus making the changing of test configurations less of a burden for the injured or handicapped.

Referring again to FIG. 2, the seat 46 may have indicia 178 formed thereon or thereabout for indicating the degree to which the seat is rotated. In addition, the seat 46 has a lever arm 182 for locking the angular position of the seat. Referring to FIG. 5, indicia 184 may be formed on the coupling member 90 to document the angular position of the load cell and horizontal arm.

Figure 10:
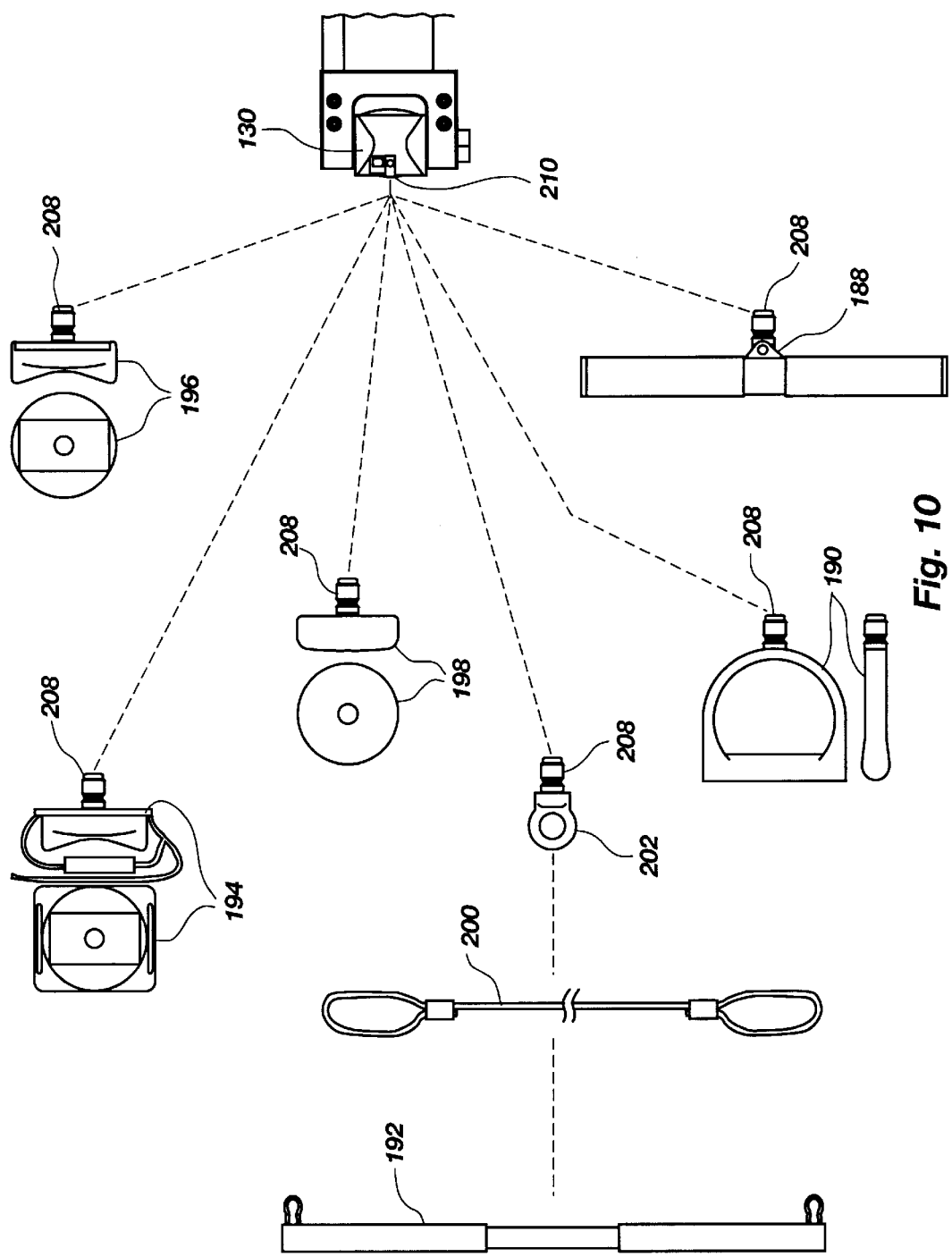
FIG. 10 is a top view of the load cell head of the presently preferred embodiment of the isometric testing apparatus of the present invention shown with various engaging devices that may be detachably coupled to the load cell head.

Referring now to FIG. 10, the load cell head 130 is shown with a plurality of engagement devices that may be detachably coupled thereto. The engaging devices are adapted to be acted upon by a body part of the patient and transmit a force applied by the patient to the device and to the load cell. The engaging devices may be configured as needed to perform the desired test. The engaging devices may have handles to grip, pads, or straps. The engaging devices may include a short bar 188, a grip handle 190, a long bar 192, a curved pad with a strap 194, a curved pad 196, and a round pad 198. In addition, other devices may be used to assist in engaging the load cell, such as a cable 200 and a ring 202.

Referring again to FIG. 6a, the load cell head 130 advantageously includes a quick connect/release fitting or coupling 206 disposed between the load cell 134 and the engagement device 186. The coupling 206 has a male fitting 208 preferably formed on the engagement device 186 and a female 210 fitting preferably formed in the load cell head 130. Referring to FIGS. 6b and 6c, a pair of arms 212 engage the female fitting 210 of the coupling 206 for releasing the coupling. The arms 212 extend out of the load cell housing 130 in a positioned suited for being activated by a user's fingers and/or thumb.

Referring again to FIG. 2, the apparatus 10 may also include a display device 216 for displaying the force information or data acquired by the load cell. The display device 216 may be a simple digital display, a monitor, or the like. The apparatus 10 may also include a data storage device 218 for recording or storing the force information. The apparatus may also include a printer device 220 or the like for creating a hard copy of the force information. The display device and storage device may be a computer 222 or microcomputer device. The computer may display the measured forces on a monitor and save the information on a computer diskette or hard drive. The computer 222 may include software for data acquisition, as is known in the industry. The software may provide instructions on how to configure the apparatus or prompt for various tests. The software may include formats for standard tests or may be customized for particular tests.

In view of the forgoing, it will be appreciated that the present invention provides an isometric testing apparatus capable of performing both seated tests, such as spinal, upper and lower extremity tests, and standing tests, such as lifting and functional tests. The present invention also provides an isometric testing apparatus which requires minimal space. The present invention also provides such an apparatus which allows the position of the patient to be easily adjusted. The present invention also provides an isometric testing apparatus capable of performing agonist/antagonist muscle tests in one patient position. The present invention also provides an isometric testing apparatus capable of creating a direct line of action between the centerline of the force measuring device and the joint line of action of the patient. The present invention also provides an isometric testing apparatus capable of providing a reproducible method of recording the position of the patient and force measuring device. The present invention also provides an isometric testing apparatus capable of providing a force measuring device with a line of action which is the same as the patient's line of action, even if the structure of the apparatus deflects during the testing. The present invention also provides an isometric testing apparatus that can be quickly customized.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An isometric testing apparatus for performing isometric strength tests on individual muscles or joints of a patient, the patient having at least a first body part and a second body part, the apparatus comprising:

a base member adapted for resting on an underlying surface and having a platform, the platform having an area upon which the patient is disposed during use, an area extending vertically therefrom defining a test area in which the patient is disposed during testing;

a force measuring device coupled to the base member and adapted to be acted upon by the first body part of the patient for measuring a force applied by the patient; and a seat adjustably coupled to the base generally opposing the force measuring device and having a seat member adapted for receiving the second body part of the patient, the seat being adjustable between at least (i) a location within the test area and in which the second body part of the patient is received in the seat member, defining a first test position, and (ii) a location outside of the testing area in which the seat does not contact the patient, defining an idle position, thereby providing for easy adjustment between testing configurations with the seat and without the seat and providing a compact testing apparatus.

2. The apparatus of claim 1, wherein the seat is adjustable to a location adjacent the test area, defining a second test position, and wherein the seat has a support surface against which the patient may push.

3. The apparatus of claim 2, wherein the seat is also pivotally coupled to the base and wherein the seat has a back member that may be positioned towards the base by pivoting the seat, the back member forming the support surface against which the patient may push.

4. The apparatus of claim 1, further comprising at least one restraining device adapted to pass around the patient and coupled to opposing sides of the seat for stabilizing the patient and isolating the muscle being tested.

5. The apparatus of claim 1, wherein the platform is horizontal, and further comprising a grid pattern and indicia formed on the horizontal platform for orienting/documenting the foot position of the patient with respect to the platform.

6. The apparatus of claim 1, wherein the seat is also pivotally coupled to the base and pivots about a vertical axis and wherein the force measuring device is rotatably coupled to the base member and rotates about a vertical axis, the seat pivoting and the force measuring device rotating to create a direct line of action between a centerline of the force measuring device and a joint line of action of the patient.

7. The apparatus of claim 1, further comprising:

an elongated vertical member coupled to the base and extending upwardly for supporting the force measuring device; and a horizontal arm adjustably coupled to the vertical member, the horizontal arm vertically adjusting along the vertical member between at least a first elevation and a second elevation for properly positioning the force measuring device, the first elevation being nearer the base and the second elevation being farther from the base, the horizontal arm horizontally adjusting along a substantially horizontal axis parallel with the horizontal arm between at least a first position and a second position for properly positioning the force measuring device, the first position being nearer the vertical member and the second position being farther from the vertical member.

8. The apparatus of claim 1, further comprising a coupling means and wherein the force measuring device is coupled to the base by the coupling means and wherein the force measuring device freely pivots in a vertical plane to compensate for any force induced deflection in the coupling means.

9. An isometric testing apparatus for performing isometric strength tests on individual muscles or joints of a patient, the patient having at least a first body part and a second body part, the apparatus comprising:

a base member adapted for resting on an underlying surface and having a platform, the platform having an area upon which the patient may be disposed, an area extending vertically therefrom defining a test area in which the patient is disposed during testing;

a force measuring device coupled to the base member and adapted to be acted upon by the first body part of the patient for measuring a force applied by the patient;

a seat adjustably coupled to the base generally opposing the force measuring device and having a seat member adapted for receiving the second body part of the patient, the seat being adjustable between at least (i) a location within the test area and in which the second body part of the patient is received in the seat member, defining a first test position, and (ii) a location outside of the testing area in which the seat does not contact the patient, defining an idle position, thereby providing for easy adjustment between testing configurations with the seat and without the seat and providing a compact testing apparatus;

an engaging device detachably coupled to the force measuring device and adapted for being acted upon by the first body part of the patient and transmitting the force applied by the patient to the force measuring device; and a quick connect/release coupling disposed between the force measuring device and the engaging device for quickly and easily coupling the engaging device to the force measuring device and providing for various other engaging devices to be quickly and easily interchanged.

10. An isometric testing apparatus for performing isometric strength tests on individual muscles or joints of a patient, the patient having at least a first body part, the apparatus comprising:

a base adapted for resting on an underlying surface upon which a patient is disposed during use;

a load cell adjustably coupled to the base and adapted for being acted upon by the first body part of the patient for measuring a force applied by the patient;

means for vertically positioning the load cell along a substantially vertical axis between at least a first elevation and a second elevation for properly positioning the load cell, the first elevation being nearer the base and the second elevation being farther from the base;

means for horizontally positioning the load cell along a substantially horizontal axis between at least a first position and a second position for properly positioning the load cell, the first position being nearer the vertical axis and the second position being farther from the vertical axis.

11. The apparatus of claim 10, wherein the means for vertically positioning the load cell and the means for horizontally positioning the load cell comprises:

an elongated vertical member coupled to the base and extending upwardly; and a horizontal arm adjustably coupled to the vertical member; and a coupler member disposed between the vertical member and the horizontal arm, the coupler sliding along the vertical member to vertically adjust the horizontal arm, and thus the load cell, the horizontal arm sliding in the coupler member to horizontally adjust the load cell.

12. The apparatus of claim 10, wherein the load cell is also rotatably coupled to the base and rotates about a vertical axis for properly positioning the load cell.

13. The apparatus of claim 12, further comprising:

a seat pivotally coupled to the base and pivoting about a vertical axis, the seat pivoting and the load cell rotating to create a direct line of action between a centerline of the force measuring device and a joint line of action of the patient.

14. The apparatus of claim 10, wherein the load cell is also pivotally coupled to the base and freely pivots in a vertical plane.

15. The apparatus of claim 10, further comprising:

a platform formed on the base with an area upon which the patient may be disposed, an area extending vertically therefrom defining a testing area in which the patient is disposed during testing; and a seat adjustably coupled to the base generally opposing the load cell and having a seat member adapted for receiving the second body part of the patient, the seat being adjustable between at least (i) a location within the test area and in which the second body part of the patient is received in the seat member, defining a first test position, and (ii) a location outside of the testing area in which the seat does not contact the patient, defining an idle position, thereby providing for easy adjustment between testing configurations with the seat and without the seat and providing a compact testing apparatus.

16. The apparatus of claim 10, further comprising a grid pattern and indicia formed on the base for orienting/ documenting a foot position of the patient with respect to the base.

17. An isometric testing apparatus for performing isometric strength tests on individual muscles or joints of a patient, the patient having at least a first body part, the apparatus comprising:

a base adapted for resting on an underlying surface upon which a patient is disposed during use;

a load cell adjustably coupled to the base and adapted for being acted upon by the first body part of the patient for measuring a force applied by the patient;

means for vertically positioning the load cell along a substantially vertical axis between at least a first elevation and a second elevation for properly positioning the load cell, the first elevation being nearer the base and the second elevation being farther from the base;

means for horizontally positioning the load cell along a substantially horizontal axis between at least a first position and a second position for properly positioning the load cell, the first position being nearer the vertical axis and the second position being farther from the vertical axis;

an engaging device detachably coupled to the load cell and adapted for being acted upon by the first body part of the patient and transmitting the force applied by the patient to the load cell; and a quick connect/release coupling disposed between the load cell and the engaging device for quickly and easily coupling the engaging device to the load cell and providing for various other engaging devices to be quickly and easily interchanged.

18. An isometric testing apparatus for performing isometric strength tests on individual muscles or joints of a patient, the patient having at least a first body part, the apparatus comprising:

a base adapted for resting on an underlying surface upon which a patient is disposed during use;

a vertical member attached to the base and extending upwardly;

a load cell adapted for being acted upon by the first body part of the patient for measuring a force applied by the patient, the load cell being pivotally coupled to the vertical member and freely pivoting in a vertical plane for compensating for deflection of the vertical member as the patient applies a force to the load cell;

a platform formed on the base with an area upon which the patient may be disposed, an area extending vertically therefrom defining a testing area in which the patient is disposed during testing; and a seat adjustably coupled to the base generally opposing the load cell and having a seat member adapted for receiving the second body part of the patient, the seat being adjustable between at least (i) a location within the test area and in which the second body part of the patient is received in the seat member, defining a first test position, and (ii) a location outside of the testing area in which the seat does not contact the patient, defining an idle position, thereby providing for easy adjustment between testing configurations with the seat and without the seat and providing a compact testing apparatus.

19. An isometric testing apparatus for performing isometric strength tests on individual muscles or joints of a patient, the patient having at least a first body part, the apparatus comprising:

a base adapted for resting on an underlying surface upon which a patient may be disposed;

a vertical member attached to the base and extending upwardly;

a load cell adapted for being acted upon by the first body part of the patient for measuring a force applied by the patient, the load cell being pivotally coupled to the vertical member and freely pivoting in a vertical plane for compensating for deflection of the vertical member as the patient applies a force to the load cell; and wherein the load cell is rotatably coupled to the base member and rotates about a vertical axis; and further comprising:

a seat pivotally coupled to the base and pivoting about a vertical axis, the seat pivoting and the load cell rotating to create a direct line of action between a centerline of the load cell and a joint line of action of the patient.

20. An isometric testing apparatus for performing isometric strength tests on individual muscles or joints of a patient, the patient having at least a first body part, the apparatus comprising:

a base adapted for resting on an underlying surface upon which a patient may be disposed;

a vertical member attached to the base and extending upwardly;

a load cell adapted for being acted upon by the first body part of the patient for measuring a force applied by the patient, the load cell being pivotally coupled to the vertical member and freely pivoting in a vertical plane for compensating for deflection of the vertical member as the patient applies a force to the load cell; and a horizontal arm adjustably coupled to the vertical member, the horizontal arm vertically adjusting along the vertical member between at least a first elevation and a second elevation for properly positioning the load cell, the first elevation being nearer the base and the second elevation being farther from the base, the horizontal arm horizontally adjusting along a substantially horizontal axis parallel with the horizontal arm between at least a first position and a second position for properly positioning the load cell, the first position being nearer the vertical member and the second position being farther from the vertical member.

21. The apparatus of claim 18, further comprising a grid pattern and indicia formed on the base for orienting/documenting a foot position of the patient with respect to the base.

22. An isometric testing apparatus for performing isometric strength tests on individual muscles or joints of a patient, the patient having at least a first body part, the apparatus comprising:

a base adapted for resting on an underlying surface upon which a patient may be disposed;

a vertical member attached to the base and extending upwardly;

a load cell adapted for being acted upon by the first body part of the patient for measuring a force applied by the patient, the load cell being pivotally coupled to the vertical member and freely pivoting in a vertical plane for compensating for deflection of the vertical member as the patient applies a force to the load cell;

an engaging device detachably coupled to the load cell and adapted for being acted upon by the first body part of the patient and transmitting the force applied by the patient to the load cell; and a quick connect/release coupling disposed between the load cell and the engaging device for quickly and easily coupling the engaging device to the load cell and providing for various other engaging devices to be quickly and easily interchanged.

23. An isometric testing apparatus for performing isometric strength tests on individual muscles or joints of a patient, the patient having at least a first body part, the apparatus comprising:

a base adapted for resting on an underlying surface upon which a patient may be disposed;

a load cell adapted for being acted upon by the first body part of the patient for measuring a force applied by the patient, the load cell being rotatably coupled to the base generally opposing the seat and rotating about a vertical axis; and an adjustable seat pivotally coupled to the base generally opposing the load cell and pivoting about a vertical axis, the seat having a seat member for receiving a second body part of the patient, the seat pivoting and the load cell rotating to create a direct line of action between a centerline of the load cell and a joint line of action of the patient.

24. The apparatus of claim 23, wherein the load cell functions in both tension and compression for agonist/antagonist testing.

25. The apparatus of claim 23, wherein the load cell freely pivots in a vertical plane to compensate for any deflection.

26. The apparatus of claim 23, further comprising:
a platform formed on the base with an area upon which the patient may be disposed, an area extending vertically therefrom defining a testing area in which the patient is disposed during testing; and
a seat adjustably coupled to the base generally opposing the load cell and having a seat member adapted for receiving the second body part of the patient, the seat being adjustable between at least (i) a location within the test area and in which the second body part of the patient is received in the seat member, defining a first test position, and (ii) a location outside of the testing area in which the seat does not contact the patient, defining an idle position, thereby providing for easy adjustment between testing configurations with the seat and without the seat and providing a compact testing apparatus.

27. The apparatus of claim 23, further comprising:
a horizontal arm adjustably coupled to the vertical member, the horizontal arm vertically adjusting along the vertical member between at least a first elevation and a second elevation for properly positioning the load cell, the first elevation being nearer the base and the second elevation being farther from the base, the horizontal arm horizontally adjusting along a substantially horizontal axis parallel with the horizontal arm between at least a first position and a second position for properly positioning the load cell, the first position being nearer the vertical member and the second position being farther from the vertical member.

28. The apparatus of claim 23, further comprising a grid pattern and indicia formed on the base for orienting/documenting a foot position of the patient with respect to the base.

29. An isometric testing apparatus for performing isometric strength tests on individual muscles or joints of a patient, the patient having at least a first body part, the apparatus comprising:
a base adapted for resting on an underlying surface upon which a patient may be disposed;
a load cell adapted for being acted upon by the first body part of the patient for measuring a force applied by the patient, the load cell being rotatable coupled to the base generally opposing the seat and rotating about a vertical axis;
an adjustable seat pivotally coupled to the base generally opposing the load cell and pivoting about a vertical axis, the seat having a seat member for receiving a second body part of the patient, the seat pivoting and the load cell rotating to create a direct line of action between a centerline of the load cell and a joint line of action of the patient;
an engaging device detachably coupled to the load cell and adapted for being acted upon by the first body part of the patient and transmitting the force applied by the patient to the load cell; and
a quick connect/release coupling disposed between the load cell and the engaging device for quickly and easily coupling the engaging device to the load cell and providing for various other engaging devices to be quickly and easily interchanged.

30. An isometric testing apparatus for performing isometric strength tests on individual muscles or joints of a patient, the patient having at least a first body part, the apparatus comprising:
a load cell adapted for measuring a force applied by the patient;
an engaging device adapted for being acted upon by the first body part of the patient and transmitting the force applied by the patient to the load cell, the engaging device being detachably coupled to the load cell; and
a quick connect/release coupling disposed between the load cell and the engaging device for quickly and easily coupling the engaging device to the load cell and providing for various other engaging devices to be quickly and easily interchanged.

31. The apparatus of claim 30, wherein the engaging device is selected from the group consisting of a handle, a short lift bar, a long lift bar, a cable, a cable and two handles, a pad, a pad and strap.

32. An isometric testing apparatus for performing isometric strength tests on individual muscles or joints of a patient, the patient having at least a first body part and a second body part, the apparatus comprising:
a base member adapted for resting on an underlying surface and having a platform, the platform having an area upon which the patient may be disposed, an area extending vertically therefrom defining a testing area in which the patient is disposed during testing;
an elongated vertical member coupled to the base and extending upwardly;
a horizontal arm adjustably coupled to the vertical member, the horizontal arm vertically adjusting along the vertical member between at least a first elevation and a second elevation for properly positioning the force measuring device, the first elevation being nearer the base and the second elevation being farther from the base, the horizontal arm horizontally adjusting along a substantially horizontal axis parallel with the horizontal arm between at least a first position and a second position for properly positioning the force measuring device, the first position being nearer the vertical member and the second position being farther from the vertical member;
a load cell adapted for being acted upon by the first body part of the patient for measuring a force applied by the patient, the load cell being rotatably coupled to the horizontal arm and rotating about a vertical axis; and
a seat adjustably coupled to the base generally opposing the force measuring device and having a seat member adapted for receiving the second body part of the patient, the seat being adjustable between at least (i) a location within the test area and in which the second body part of the patient is received in the seat member, defining a first test position, and (ii) a location outside of the testing area in which the seat does not contact the patient, defining an idle position, the seat pivoting and the load cell rotating to create a direct line of action between a centerline of the load cell and a joint line of action of the patient, thereby providing for easy adjustment between testing configurations with the seat and without the seat and providing a compact testing apparatus.

33. The apparatus of claim 32, further comprising a display device for displaying the force measured by the load cell.

34. The apparatus of claim 32, further comprising a data storage device for storing the force measured by the load cell.

35. The apparatus of claim 32, further comprising a printer device for creating a hard copy of the force measured by the load cell.

36. The apparatus of claim 32, further comprising a microcomputer device for displaying and storing the force measured by the load cell.

37. The apparatus of claim 36, further comprising a software program that prompts for test configurations.

38. The apparatus of claim 32, wherein the load cell functions in both tension and compression for agonist/antagonist testing.

39. The apparatus of claim 32, further comprising at least one restraining device adapted to pass around the patient and coupled to opposing sides of the seat for stabilizing the patient and isolating the muscle being tested.

40. The apparatus of claim 32, further comprising a grid pattern and indicia formed on the base for orienting/documenting a foot position of the patient with respect to the base.

41. The apparatus of claim 32, further comprising:
- an engaging device detachably coupled to the load cell and adapted for being acted upon by the first body part of the patient and transmitting the force applied by the patient to the load cell; and
- a quick connect/release coupling disposed between the load cell and the engaging device for quickly and easily coupling the engaging device to the load cell and providing for various other engaging devices to be quickly and easily interchanged.

* * * * *